United States Patent
Wang

(10) Patent No.: US 10,856,728 B2
(45) Date of Patent: *Dec. 8, 2020

(54) TRACHEOSCOPE CATHETER BENDING STRUCTURE

(71) Applicant: Zhuhai Kaden Medical Imaging Technology Co., Ltd, Zhuhai (CN)

(72) Inventor: Nanbing Wang, Guangdong (CN)

(73) Assignee: Zhuhai Kaden Medical Imaging Technology Co., Ltd, Zhuhai (CN)

( * ) Notice: Subject to any disclaimer, the term of this patent is extended or adjusted under 35 U.S.C. 154(b) by 308 days.

This patent is subject to a terminal disclaimer.

(21) Appl. No.: 15/879,537

(22) Filed: Jan. 25, 2018

(65) Prior Publication Data
US 2018/0206706 A1    Jul. 26, 2018

(30) Foreign Application Priority Data

Jan. 25, 2017    (TW) .............................. 106102869 A
Jan. 25, 2017    (TW) .............................. 106201406 U

(51) Int. Cl.
| | |
|---|---|
| *A61B 1/005* | (2006.01) |
| *A61M 25/01* | (2006.01) |
| *A61B 1/267* | (2006.01) |
| *A61B 1/012* | (2006.01) |
| *A61B 1/06* | (2006.01) |
| *A61M 16/04* | (2006.01) |

(52) U.S. Cl.
CPC ............ *A61B 1/0052* (2013.01); *A61B 1/005* (2013.01); *A61B 1/0055* (2013.01); *A61B 1/267* (2013.01); *A61B 1/012* (2013.01); *A61B 1/0676* (2013.01); *A61M 16/0472* (2013.01); *A61M 25/0138* (2013.01); *A61M 25/0147* (2013.01); *A61M 2025/015* (2013.01)

(58) Field of Classification Search
CPC ........ A61M 16/0472; A61M 2025/015; A61M 25/0138; A61M 25/0147; A61B 1/005; A61B 1/0052; A61B 1/0055; A61B 1/012; A61B 1/0676; A61B 1/267
See application file for complete search history.

(56) References Cited

U.S. PATENT DOCUMENTS

| | | | | |
|---|---|---|---|---|
| 4,846,573 A | * | 7/1989 | Taylor .................. | A61B 1/0053 356/241.4 |
| 4,873,965 A | * | 10/1989 | Danieli ................ | A61B 1/0055 600/141 |

(Continued)

FOREIGN PATENT DOCUMENTS

CN            104902801 A       9/2015

*Primary Examiner* — Quynh-Nhu H. Vu

(57) ABSTRACT

The tracheoscope catheter bending structure mainly includes a main elastic spring ring, two small elastic spring rings and a fixed seat, wherein the main elastic spring ring is arranged inside a hose at the far end of a tracheoscope catheter; the two small elastic spring rings are arranged at the internal opposite two side positions of the main elastic spring ring; two pull wires provided for a tracheoscope are respectively penetrated through the two small elastic spring rings; the fixed seat is held at the farthest end of the hose; the far ends of the two pull wires respectively pass through penetration holes at the two sides of the fixed seat and are fixed; the other ends of the pull wires are extended and are combined with a control mechanism inside a handle.

2 Claims, 3 Drawing Sheets

(56) References Cited

U.S. PATENT DOCUMENTS

| | | | | |
|---|---|---|---|---|
| 5,002,041 | A * | 3/1991 | Chikama | A61B 1/0055 600/139 |
| 5,005,558 | A * | 4/1991 | Aomori | A61B 1/0055 600/141 |
| 5,176,126 | A * | 1/1993 | Chikama | A61B 1/0055 138/120 |
| 5,179,935 | A * | 1/1993 | Miyagi | A61B 1/0055 600/108 |
| 5,271,381 | A * | 12/1993 | Ailinger | A61B 1/0055 138/120 |
| 9,357,984 | B2 * | 6/2016 | Malkowski | A61B 17/00234 |
| 10,561,822 | B2 * | 2/2020 | Wang | A61B 1/0052 |
| 2005/0131279 | A1 * | 6/2005 | Boulais | A61B 1/0052 600/141 |
| 2009/0209815 | A1 * | 8/2009 | Smith | A61B 1/0055 600/114 |
| 2013/0281924 | A1 * | 10/2013 | Shellenberger | A61B 17/00234 604/95.01 |
| 2014/0058324 | A1 * | 2/2014 | Salahieh | A61M 25/0144 604/95.04 |
| 2014/0200595 | A1 * | 7/2014 | Kortenbach | A61B 17/0643 606/139 |
| 2016/0151122 | A1 * | 6/2016 | Alvarez | A61B 17/00234 604/95.04 |
| 2017/0007224 | A1 * | 1/2017 | Sholev | A61B 1/0057 |
| 2017/0290493 | A1 * | 10/2017 | Cohen | A61M 25/0045 |

* cited by examiner

TRACHEOSCOPE CATHETER BENDING STRUCTURE

CROSS REFERENCE TO RELATED APPLICATIONS

The present application claims the benefit of Taiwanese Patent Application Nos. 106201406 and 106102869 filed on Jan. 25, 2017. All the above are hereby incorporated by reference.

TECHNICAL FIELD

The invention is a tracheoscope catheter bending structure, and mainly provides an innovative bending structure which can simply control the far end of a catheter to swing in the catheter of a tracheoscope by cooperation of multiple elastic spring rings and pull wires and has progressive practicability.

BACKGROUND

A tracheoscope generally includes an elongated catheter so as to extend into a human body. The far end of the catheter is combined with a shooting module, so as to shoot an image in a human body cavity and send the image to an external screen, and therefore a medical staff observes or gives treatment directly. In order to get images at different angular positions inside the human body, a hose structure that may be bent is arranged at the far end of the catheter, so as to control the hose to swing and link the shooting module to rotate, thereby obtaining multiple intracavitary images at different angles.

A common bending structure is provided with multiple riveted units inside the hose at the far end of the catheter to form a structure capable of swinging laterally. To provide a hose at the far end of the bent catheter, a well-known unit a1 structure as shown in FIG. 1, the two sides of a cylindrical body a11 is respectively provided with a combination piece a12; by riveting two combination pieces a12 of one unit a1 with the cylindrical body a11 of the other unit a1 via a micro rivet a13 or riveting using laser welding, then combining the multiple units in sequence, arranging inside the hose at the far end of the catheter and cooperating with driving of the two pull wires, the purpose of bending is achieved. Although in such a manner, the far end of the catheter can be swung by means of the structure of riveting each unit, but the procedure of riveting each unit is very troublesome and difficult. Moreover, for each catheter, there is a need to combine multiple units. Thus, the manufacturing is not convenient enough and there is an improved space.

Additionally, there is the conventional art having Chinese patent application No. 201380069722.6 titled "Hinged End Part for Endoscope". Herein, the hinged units can be buckled one another into a bendable structure, and the far end of a pipe provided for the endoscope can be controlled to swing. Although the structure of the combined unit is relatively simple, the machining cost is high. There is a need to combine the units one by one, being not convenient enough. In application, for swinging and bending among the units, if there is any poor performance, an unrepairable fault may be caused and thus it is necessary to make improvements.

SUMMARY

The invention is a tracheoscope catheter bending structure, and mainly provides an innovative bending structure. The tracheoscope catheter bending structure is applied to the inside of a catheter of a body tracheoscope and has better progress and practicability.

The objectives of the invention are implemented by the following technical solutions.

A tracheoscope catheter bending structure includes a main elastic spring ring, two small elastic spring rings and a fixed seat, wherein the main elastic spring ring is arranged inside a hose which is located at the far end of a tracheoscope catheter; the two small elastic spring rings are arranged at the internal two opposite side positions of the main elastic spring ring; two pull wires of a tracheoscope are respectively penetrated through the two small elastic spring rings; the fixed seat is held at the farthest end of the hose; the fixed seat is provided with a central vertical plate; multiple penetration holes are formed at the two sides of the central vertical plate; the far ends of the two pull wires respectively pass through middle penetration holes at the two sides of the central vertical plate of the fixed seat and are fixed by positioning plates. Therefore, by applying a force to different pull wires, the fixed seat can be linked to swing to a corresponding one side, thereby achieving the purposes of controlling the far end of the catheter to laterally swing and bend and obtaining obvious progress.

Reference Numbers are Set Forth Hereinafter:

1 a main elastic spring ring; 2 a small elastic spring ring; 3 a fixed seat; 31 a central vertical plate; 32 a penetration hole; 33 a fixed plate; 4 a catheter; 5 a pull wire; 6 a fixed seat; 61 a central opening; 62 a penetration hole; 63 a directing strip

DETAILED DESCRIPTION OF THE EMBODIMENTS

Figure 1:
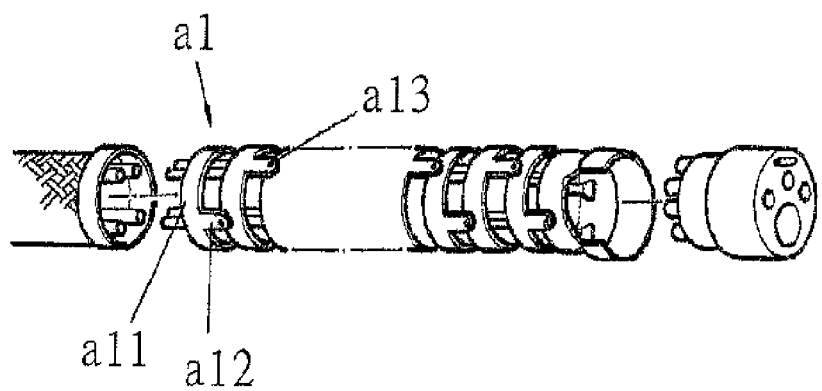
FIG. 1 is a combined diagram of a tracheoscope catheter unit structure of the conventional art.
Figure 2:
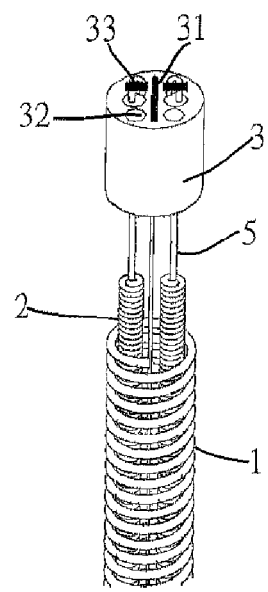
FIG. 2 is a stereoscopic diagram of a tracheoscope catheter bending structure of the invention.
Figure 3:
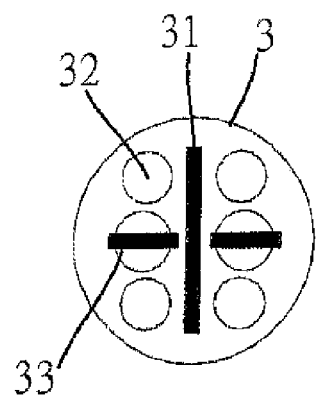
FIG. 3 is a plane diagram of a far end of FIG. 2 of the invention.

Please referring to FIG. 2 and FIG. 3, the embodiment is a tracheoscope catheter bending structure, which mainly includes a main elastic spring ring 1, two small elastic spring rings 2 and a fixed seat 3, wherein the main elastic spring ring 1 is arranged inside a hose at the far end of a tracheoscope catheter 4; the outer diameter of the main elastic spring ring 1 is smaller than the inner diameter of the catheter 4; the two small elastic spring rings 2 are arranged at the internal opposite two side positions of the main elastic spring ring 1; two pull wires 5 provided for a tracheoscope are respectively penetrated through the two small elastic spring rings 2; the fixed seat 3 is arranged at the farthest end of the catheter 4; the fixed seat is provided with a central vertical plate 31; multiple penetration holes 32 are formed at the two sides of the central vertical plate 31; the far ends of the two pull wires 5 respectively pass through middle penetration holes at the two sides of the central vertical plate 31 of the fixed seat 3 and are respectively fixed by a positioning plate 33, thereby finishing a bendable structure of the invention. Power wires and connection wires can be arranged in other penetration holes on the fixed seat 3 in the penetration manner, so as to connect a shooting module and luminophors at the far end as well as a control mechanism and a power mechanism at the near end.

Figure 4:
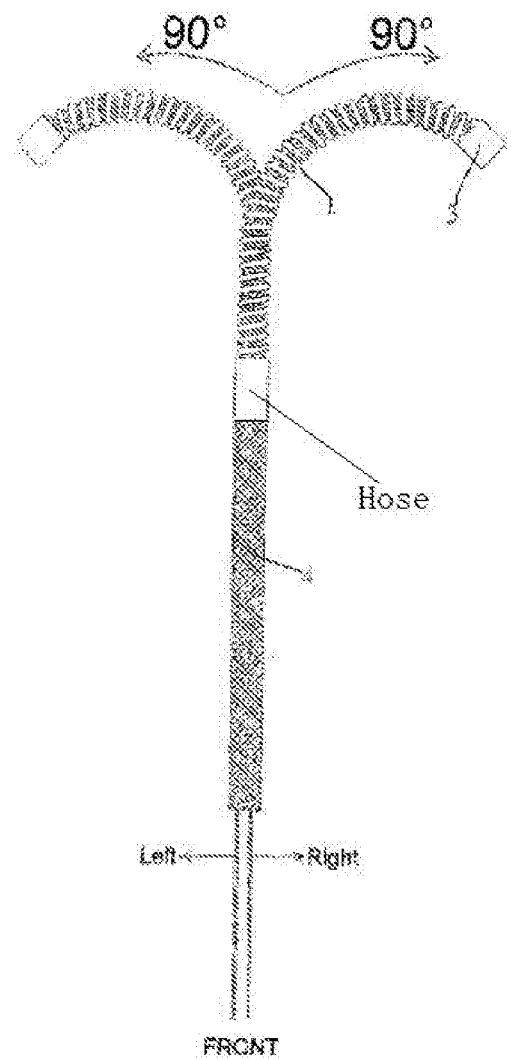
FIG. 4 is a systematic diagram for swinging a catheter of the invention.

When the tracheoscope catheter bending structure is used, the main elastic spring ring 1 and the small elastic spring rings 2 have the bendability in itself, so by applying a force to different pull wires 5, the positioning plates 33 at the far ends of the pull wires 5 can link the fixed seat 3 to swing to a corresponding direction. With the separation of the central vertical plate 31, the fixed seat 3 can guarantee that it only can bend and incline to the two sides of the central vertical plate 31, thereby achieving the purposes of controlling a hose portion at the far end of the catheter, stabilizing the state of swinging toward the two sides as shown in FIG. 4 and enabling the far end of the catheter 4 to bend; and thus, it has significant progress.

Figure 5:
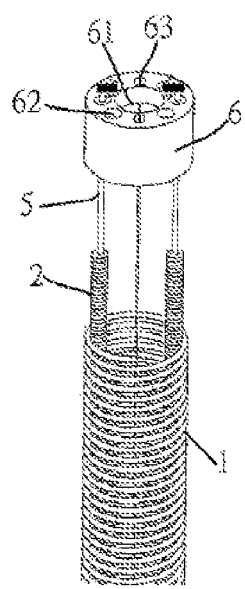
FIG. 5 is a stereoscopic diagram of another embodiment of the invention.

Please referring to FIG. 5 again, it is a changed embodiment of the invention, wherein the fixed seat 6 is provided with a central opening 61, and is provided with a plurality of the penetration holes 62 on an annular external portion; the central opening 61 can be used for connecting a pipe to form a working channel; the far ends of the two pull wires 5 are also respectively arranged in two penetration holes at opposite sides of the fixed seat 6 in a penetration manner; a directing strip 63 is arranged in each of the two penetration holes at the other two sides of the two pull wires 16; the fixed seat 6 can be bent accurately toward a corresponding direction under the linkage of the different pull wires 2, and the hose portion at the far end of the catheter is driven to bend and swing. Hence, the invention increases the application range and improves the practicability.

In conclusion, according to the improved bending structure of the invention, the manufacturing process is simple; the multiple units do not need to be buckled or riveted and pivoted for multiple times and can be simply combined inside the hose at the far end of the pipe, thereby achieving the purpose of simply controlling the far end of the tracheoscope catheter to bend and swing; and thus, the invention apparently has excellent practicability and progress compared with the well-known design.

What is claimed is:

1. A tracheoscope catheter bending structure, comprising:
   a main elastic spring ring, two small elastic spring rings and a fixed seat, wherein
   the main elastic spring ring is arranged inside a hose located at a far end of a catheter of a tracheoscope; an outer diameter of the main elastic spring ring is slightly smaller than an inner diameter of the catheter;
   the two small elastic spring rings are arranged at internal two opposite side positions of the main elastic spring ring; two pull wires of the tracheoscope are respectively penetrated through the two small elastic spring rings; and
   the fixed seat is combined at a farthest end of the hose and is provided with multiple penetration holes penetrating the fixed seat along a direction parallel to the pulling wires; far ends away from the two small elastic spring rings of the two pull wires respectively pass through two penetration holes and are respectively fixed by a positioning plate.

2. The tracheoscope catheter tending structure as claimed in claim 1, wherein the fixed seat is provided with a central vertical plate; the penetration holes are arranged at two sides of the central vertical plate, such that the far ends of the two pull wires respectively pass through a middle of the penetration holes at the two sides of the central vertical plate of the fixed seat.

* * * * *